US009211062B2

(12) United States Patent
Sakagawa et al.

(10) Patent No.: US 9,211,062 B2
(45) Date of Patent: Dec. 15, 2015

(54) OPTICAL COHERENCE TOMOGRAPHIC IMAGING APPARATUS AND METHOD FOR CONTROLLING THE SAME

(71) Applicant: CANON KABUSHIKI KAISHA, Tokyo (JP)

(72) Inventors: Wataru Sakagawa, Kawasaki (JP); Yukio Sakagawa, Tokyo (JP); Shigeaki Ono, Tokyo (JP); Hiroki Uchida, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 29 days.

(21) Appl. No.: 14/161,498

(22) Filed: Jan. 22, 2014

(65) Prior Publication Data

US 2014/0211155 A1    Jul. 31, 2014

(30) Foreign Application Priority Data

Jan. 31, 2013  (JP) ................... 2013-017661

(51) Int. Cl.
| | |
|---|---|
| A61B 3/14 | (2006.01) |
| A61B 3/10 | (2006.01) |
| A61B 3/00 | (2006.01) |
| A61B 3/113 | (2006.01) |
| A61B 3/12 | (2006.01) |
| A61B 3/15 | (2006.01) |

(52) U.S. Cl.
CPC .............. *A61B 3/102* (2013.01); *A61B 3/113* (2013.01); *A61B 3/12* (2013.01); *A61B 3/152* (2013.01)

(58) Field of Classification Search
USPC .................................. 351/200–246
See application file for complete search history.

(56) References Cited

U.S. PATENT DOCUMENTS

| | | | |
|---|---|---|---|
| 8,668,335 B2 * | 3/2014 | Satake ................ | 351/206 |
| 2008/0024721 A1 | 1/2008 | Ueno et al. | |
| 2011/0267581 A1 | 11/2011 | Nakajima et al. | |
| 2012/0033181 A1 | 2/2012 | Koizumi et al. | |
| 2013/0003018 A1 * | 1/2013 | Utagawa et al. ........ | 351/206 |
| 2014/0068513 A1 * | 3/2014 | Sakagawa ............ | 715/810 |

FOREIGN PATENT DOCUMENTS

| | | |
|---|---|---|
| CN | 101133943 A | 3/2008 |
| CN | 102058391 A | 5/2011 |
| CN | 102209488 A | 10/2011 |
| JP | 2008029467 A | 2/2008 |
| JP | 2011-092291 A | 5/2011 |
| JP | 2012-000266 A | 1/2012 |
| WO | 2011/139895 A1 | 11/2011 |

* cited by examiner

*Primary Examiner* — Mohammed Hasan
(74) *Attorney, Agent, or Firm* — Canon USA Inc. IP Division

(57) ABSTRACT

An optical coherence tomographic imaging apparatus includes a movement amount acquisition unit configured to acquire the amount of subject's eye movement based on a plurality of images of the subject's eye acquired at different times, a determination unit configured to determine whether the amount of subject's eye movement before a scan by the scanning unit exceeds a threshold value, and a control unit configured to, in a case the amount of subject's eye movement before the scan is equal to or smaller than the threshold value, control the scanning unit to perform scanning position correction between a scan and the next scan based on the amount of movement.

20 Claims, 17 Drawing Sheets

OPTICAL COHERENCE TOMOGRAPHIC IMAGING APPARATUS AND METHOD FOR CONTROLLING THE SAME

BACKGROUND OF THE INVENTION

1. Field of the Invention

The present invention relates to an optical coherence tomographic imaging apparatus for capturing a tomographic image of a subject's eye through optical coherence, and a method for controlling the optical coherence tomographic imaging apparatus.

2. Description of the Related Art

A presently known optical coherence tomographic imaging apparatus based on optical coherence tomography (OCT) utilizes multi-wavelength light wave interference. For example, the optical coherence tomographic imaging apparatus is used to acquire internal organ information with an endoscope and retina information in an ophthalmologic apparatus, and applied to increasing number of fields in the human body. An optical coherence tomographic imaging apparatus applied to the human eye is becoming essential for specialized retina clinic, as an ophthalmologic apparatus.

Such an optical coherence tomographic imaging apparatus is capable of irradiating a sample with measuring light which is low-coherent light, and measuring backward scattering light from the sample by using an interferometer. In a case one point on the sample is irradiated with the measuring light, image information in a depth direction at the one point on the sample can be acquired. Further, by performing measurement while scanning the sample with the measuring light, a tomographic image of the sample can be acquired. In a case the optical coherence tomographic imaging apparatus is applied to the fundus, the fundus of the subject's eye is scanned with the measuring light to capture a high-resolution tomographic image of the fundus of the subject's eye. Therefore, the optical coherence tomographic imaging apparatus is widely used in ophthalmology diagnosis of the retina.

Generally, the optical coherence tomographic imaging apparatus uses a method for capturing a plurality of tomographic images by repetitively scanning a measurement target (fundus), in a horizontal or vertical direction. Thus, the optical coherence tomographic imaging apparatus scans an identical region on the fundus a plurality of times to capture a plurality of tomographic images of the identical region, and performs averaging processing on the captured tomographic images to acquire a high-definition tomographic image of the fundus. Further, by scanning the fundus a plurality of times while moving the scanning position in parallel, a three-dimensional image of the fundus can be acquired. In a case scanning the fundus a plurality of times in this way, however, since it takes a certain amount of time to complete image capturing, the eye may move during image capturing.

Japanese Patent Application Laid-Open No. 2008-29467 discusses an ophthalmologic imaging apparatus having a tracking function. Specifically, the ophthalmologic imaging apparatus successively captures a plurality of front images of the subject's eye, detects the subject's eye movement by using the plurality of acquired front images, and corrects scanning positions according to the subject's eye movement.

SUMMARY OF THE INVENTION

According to an aspect of the present invention, an optical coherence tomographic imaging apparatus includes an image acquisition unit configured to acquire a plurality of images of a subject's eye at different times, a tomographic image acquisition unit configured to acquire a plurality of tomographic images of the subject's eye based on an interference light produced by the interference between return light from the subject's eye irradiated with measuring light via a scanning unit, and reference light corresponding to the measuring light, a movement amount acquisition unit configured to acquire the amount of subject's eye movement based on the plurality of images, a determination unit configured to determine whether the amount of subject's eye movement before a scan by the scanning unit exceeds a threshold value, and a control unit configured to, in a case where the amount of subject's eye movement before the scan is equal to or smaller than the threshold value, control the scanning unit to perform scanning position correction between the scan and the next scan based on the amount of movement.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Figure 1:
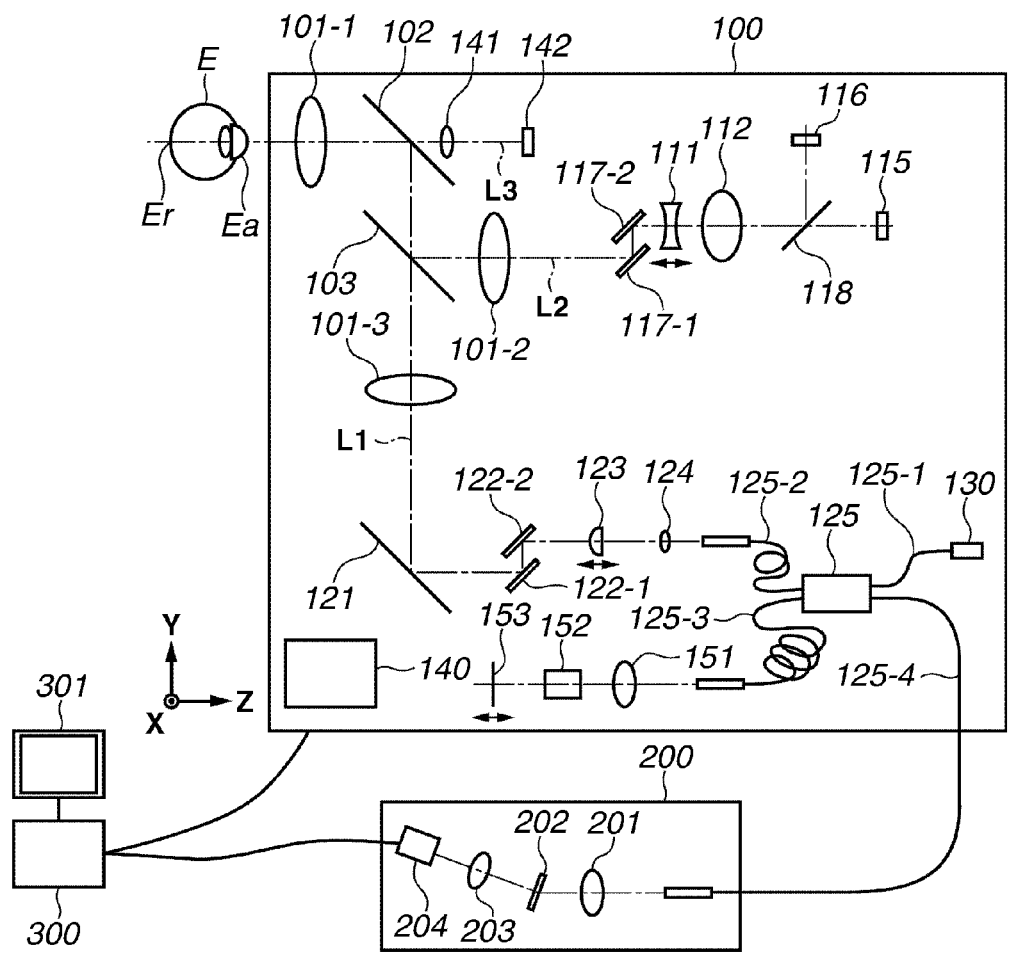
FIG. 1 illustrates an example of a configuration of an optical coherence tomographic imaging apparatus according to a first exemplary embodiment.

Various exemplary embodiments, features, and aspects of the invention will be described in detail below with reference to the drawings.

Generally, there is a time lag from when the subject's eye movement is detected till when scanning position correction is performed. Therefore, in a case where there arises a comparatively large subject's eye movement per unit time (such as a flick movement which is one of involuntary eye movements during fixation), a distortion will arise by this movement in a tomographic image even if this movement is tracked. Further, the distortion will arise also in correcting a scanning position deviation due to this movement.

One of objectives of the present exemplary embodiment is to acquire a tomographic image with reduced distortion due to this movement even if there arises a comparatively large subject's eye movement per unit time during tracking of the subject's eye movement.

The optical coherence tomographic imaging apparatus according to the present exemplary embodiment can acquire the amount of subject's eye movement (for example, the amount of subject's eye rotation) based on a plurality of images of the subject's eye (for example, a plurality of fundus images) acquired at different times. The optical coherence tomographic imaging apparatus according to the present exemplary embodiment can determine whether the amount of subject's eye movement before a scan by a scanning unit exceeds a threshold value. In a case the amount of subject's eye movement before the scan is equal to or smaller than the threshold value, the optical coherence tomographic imaging apparatus according to the present exemplary embodiment can control the scanning unit to perform scanning position correction between the scan and the next scan based on the amount of subject's eye movement.

An optical coherence tomographic imaging apparatus according to another exemplary embodiment can control the scanning unit, in a case where the amount of subject's eye movement before the scan exceeds a threshold value, to restart scan of the scanning unit from a scanning position before the scan.

An optical coherence tomographic imaging apparatus according to still another exemplary embodiment can detect a blink of the subject's eye before a scan by the scanning unit, based on a plurality of images of the subject's eye acquired at different times. An optical coherence tomographic imaging apparatus according to still another exemplary embodiment can control the scanning unit, in a case where a blink of the subject's eye is detected, to restart scan of the scanning unit from a scanning position before the scan.

An optical coherence tomographic imaging apparatus according to still another exemplary embodiment can control the scanning unit (control the operation of a unit for tracking the subject's eye) to perform scanning position correction between a scan and the next scan of the scanning unit based on a plurality of images of the subject's eye acquired at different times.

According to at least one of the above-described exemplary embodiments, it is possible to acquire a tomographic image by reducing distortion due to the relevant subject's movement, even in a case where a comparatively large subject's eye movement per unit time arises.

In a case fundus tracking is activated during tomographic image capturing, a distortion may arise in a tomographic image due to correction of a scanning position through fundus tracking. In a case the interval of scanning position correction through fundus tracking is shorter than the time for acquiring information in the depth direction (A scan acquisition time) at one point on the subject's eye, no distortion arises in the tomographic image because the scanning position correction is suitably performed at each scanning point for acquiring one tomographic image. However, it is difficult to make the interval of scanning position correction through fundus tracking shorter than the A scan acquisition time. For example, in fundus tracking, since a front fundus image is often used, it is difficult to make the interval of scanning position correction through fundus tracking shorter than a front image acquisition interval. Generally, the front image acquisition interval is about several tens of milliseconds which are longer than the A scan acquisition interval (generally, several tens of microseconds). Therefore, it is difficult to perform scanning position correction through fundus tracking for each point during scan on the subject's eye. Scanning position correction is performed at regular intervals for each amount of scanning range. After scanning position correction is performed at regular intervals, eye movements detected at regular intervals will be corrected at one time. As a result, in a case where scan is performed on the subject's eye, a rapid change in the scanning position will be produced at regular intervals. Such a rapid change in the scanning position appears as a tomographic deviation (distortion) at regular intervals on a captured tomographic image.

Such a tomographic image distortion not only disturbs image diagnosis by a doctor but also causes misrecognition of the tomographic image distortion as a lesioned portion, possibly leading to misdiagnosis. Further, a tomographic image distortion may also have an adverse effect on an automatic retina layer boundary recognition function provided in many optical coherence tomographic imaging apparatuses. If a retina layer boundary is misrecognized, measurement values of the retina layer thickness based on the misrecognition will be displayed, possibly leading to misdiagnosis.

To avoid this problem, it is desirable to control the method for tracking the relevant subject's eye in a case where a plurality of tomographic images of the subject's eye is acquired. This enables acquiring tomographic images with reduced distortion due to the subject's eye movement. For example, it is desirable to activate the means for tracking the subject's eye so as to correct the acquisition position of the next tomographic image between the time when one of a plurality of tomographic images is acquired and the time when the next tomographic image is acquired.

In a case where automatic alignment for automatically adjusting the relative positional relation between the subject's eye and an optical storage unit is activated during capturing of a tomographic image, a similar distortion may arise in the tomographic image. In this case, the eccentricity of the image capturing optical axis due to automatic alignment may incline or vertically move the retina on the tomographic image. In particular, in a case where performing scan a plurality of times to acquire a plurality of tomographic images, there arises a situation where the retina is horizontally located in a certain tomographic image, however, inclined in another tomographic image. In a case a plurality of tomographic images having different inclinations is captured in this way, a difference in inclination between tomographic images appears as a retina shape distortion on a three-dimensional image generated from the plurality of tomographic images.

The above-described factors will specifically be described in the following exemplary embodiments.

A first exemplary embodiment will be described below with reference to the accompanying drawings.

(Overall Configuration of Optical Coherence Tomographic Imaging Apparatus)

The following describes an overall configuration of an optical coherence tomographic imaging apparatus according to a first exemplary embodiment, with reference to FIG. 1. The optical coherence tomographic imaging apparatus according to the present exemplary embodiment acquires a tomographic image of the subject's eye based on an interference light produced by the interference between return light from the subject's eye, irradiated with measuring light via a scanning unit, and reference light corresponding to the measuring light. The optical coherence tomographic imaging apparatus includes an optical head unit 100, a spectroscope 200, and a control unit 300. The following describes the configurations of the optical head unit 100, the spectroscope 200, and the control unit 300 in this order.

(Configurations of Optical Head Unit 100 and Spectroscope 200)

The optical head unit 100 includes a measuring light optical system for capturing a two-dimensional image and a tomographic image of an anterior ocular segment Ea and a fundus Er of a subject's eye E. The following describes the inside of the optical head unit 100. An objective lens 101-1 is disposed to face the subject's eye E. The optical path is branched by a first dichroic mirror 102 and a second dichroic mirror 103 disposed on the optical axis to function as an optical path separation unit. Specifically, the optical path is branched for each wavelength band into a measurement path L1 of an OCT optical system, a fundus observation optical path and a fixation lamp optical path L2, and an anterior ocular segment observation optical path L3.

The optical path L2 is further branched for each wavelength band by a third dichroic mirror 118 into an optical path to an avalanche photodiode (APD) 115 for fundus observation, and an optical path to a fixation lamp 116. Lenses 101-2, 111, and 112 are disposed on the optical path L2. The lens 111 is driven by a motor (not illustrated) for focusing adjustment for the fixation lamp and fundus observation. The APD 115 has sensitivity in the vicinity of the wavelength of illumination light for fundus observation (not illustrated), specifically, 780 nanometers. The fixation lamp 116 generates visible light to prompt the subject to perform the fixation.

An X scanner 117-1 (for the main scanning direction) and a Y scanner 117-2 (for the sub scanning direction intersecting with the main scanning direction) for scanning the fundus Er of the subject's eye E with light emitted from an illumination light source for fundus observation (not illustrated) are disposed on the optical path L2. The lens 101-2 is disposed so that its focal position comes to the vicinity of the center position between the X scanner 117-1 and the Y scanner 117-2. Although the X scanner 117-1 is a resonance type mirror, it may be a polygon mirror. The vicinity of the center position between the X scanner 117-1 and the Y scanner 117-2 has an optically conjugate relation with the pupillary position of the subject's eye E. The APD 115 (single detector) detects light dispersed and reflected by the fundus Er, as return light. The third dichroic mirror 118, which is a prism composed of a perforated mirror or a vapor-deposited hollow mirror, separates incident light into the illumination light and the return light from the fundus Er.

A lens 141 and an infrared charge-coupled device (CCD) 142 for anterior ocular segment observation are disposed on the optical path L3. The infrared CCD 142 has sensitivity in the vicinity of the wavelength of illumination light for anterior ocular segment observation (not illustrated), specifically, 970 nanometers. The optical path L1 forms the OCT optical system, as described above, and is used to capture a tomographic image of the fundus Er of the subject's eye E. More specifically, the optical path L1 is used to acquire an interference signal for forming a tomographic image.

A lens 101-3, a mirror 121, and an X scanner 122-1 and a Y scanner 122-2 as a scanning unit are disposed on the optical path L1 to deflect light on the fundus Er of the subject's eye E. Further, the X scanner 122-1 and the Y scanner 122-2 are disposed so that the center position between the X scanner 122-1 and the Y scanner 122-2 comes to the focal position of the lens 101-3. Further, the vicinity of the center position between the X scanner 122-1 and the Y scanner 122-2 has an optically conjugate relation with the pupillary position of the subject's eye E. With this configuration, the optical paths having the scanning unit as an object point become approximately parallel between the lenses 101-1 and 101-3. This enables providing an identical incident angle for the first dichroic mirror 102 and the second dichroic mirror 103 even when the X scanner 122-1 and the Y scanner 122-2 perform scanning.

A measuring light source 130 serves as a light source for emitting the measuring light into the measurement path. According to the present exemplary embodiment, the measuring light source 130 is a fiber end, and has an optically conjugate relation with the fundus Er of the subject's eye E. Lenses 123 and 124 are disposed on the optical path L1. The lens 123 is driven by a motor (not illustrated) to perform focusing adjustment. Focusing adjustment is performed so that the light emitted from the measuring light source 130 (fiber end) is focused on the fundus Er. The lens 123 which functions as a focusing adjustment unit is disposed between the measuring light source 130 and the X scanner 122-1 and the Y scanner 122-2 as a scanning unit. This makes it unnecessary to move the larger lens 101-3 and an optical fiber 125-2.

This focusing adjustment enables forming of an image of the measuring light source 130 on the fundus Er of the subject's eye E, and the return light can be efficiently returned from the fundus Er of the subject's eye E to the optical fiber 125-2 via the measuring light source 130.

Referring to FIG. 1, although the optical path between the X scanner 122-1 and the Y scanner 122-2 is formed within the drawing paper, it is actually formed in the direction perpendicular to the drawing paper. The optical head unit 100 further includes a head driving unit 140. The head driving unit 140 includes three motors (not illustrated) to enable moving of the optical head unit 100 in the three-dimensional (X, Y, Z) directions with respect to the subject's eye E. Thus, the optical head unit 100 can be aligned with respect to the subject's eye E.

The following describes the configurations of the optical path from the measuring light source 130, a reference light optical system, and the spectroscope 200. The measuring light source 130, an optical coupler 125, optical fibers 125-1 to 125-4, a lens 151, a dispersion compensation glass 152, a mirror 153, and a spectroscope 200 form a Michelson interference system. The optical fibers 125-1 to 125-4 (single mode optical fibers) are connected to and integrated with the optical coupler 125.

The light emitted from the measuring light source 130 advances through the optical fiber 125-1, and is divided into measuring light on the side of the optical fiber 125-2 and reference light on the side of the optical fiber 125-3 by the optical coupler 125. The measuring light advances through the above-described optical path of the OCT optical system. The fundus Er of the subject's eye E (observation target) is irradiated with the measuring light. Then, after the reflection and dispersion on the retina, the measuring light reaches the optical coupler 125 via the same optical path.

On the other hand, the reference light advances through the optical fiber 125-3, the lens 151, the dispersion compensation glass 152 provided to join dispersion of the measuring light and the reference light, reaches the mirror 153, and reflects off the mirror 153. Then, the reference light advances through the same optical path, and reaches the optical coupler 125. The optical coupler 125 combines the measuring light and the reference light into interference light. In this case, interference occurs when the optical path length for the measuring light becomes almost identical to the optical path length for the reference light. The position of the mirror 153 is adjustably held in the optical axis direction by a motor and a drive mechanism (not illustrated), enabling adjusting of the optical path length of the reference light to the optical path length of the measuring light which changes according to the subject's eye E. The interference light is led to the spectroscope 200 via the optical fiber 125-4.

The spectroscope 200 includes a lens 201, a diffraction grating 202, a lens 203, and a line sensor 204. The interference light emitted from the optical fiber 125-4 is converted into approximately parallel light by the lens 201, subjected to spectral diffraction by the diffraction grating 202, and then focused on the line sensor 204 by the lens 203.

The following describes the periphery of the measuring light source 130. The measuring light source 130, a typical low-coherent light source, is a super luminescent diode (SLD) having a center wavelength of 855 nanometers and a wavelength bandwidth of about 100 nanometers. The bandwidth affects the resolution of an acquired tomographic image in the optical axis direction, and therefore serves as an important parameter. Further, although a SLD is selected as a light source, the light source type is not limited thereto and may be, for example, an amplified spontaneous emission (ASE) as long as low-coherent light can be emitted. In consideration of ocular measurement, the near-infrared light is suitable for the center wavelength. Since the center wavelength affects the resolution of an acquired tomographic image in the horizontal direction, the center wavelength is desirably as short as possible. For both reasons, the center wavelength was set to 855 nanometers.

Although, in the present exemplary embodiment, a Michelson interferometer is used as an interferometer, a Mach-Zehnder interferometer may also be used. In a case the light volume difference between the measuring light and the reference light is large, the use of a Mach-Zehnder interferometer is desirable. In a case a light volume difference is comparatively small, the use a Michelson interferometer is desirable.

(Configuration of Control Unit 300)

The control unit 300 is connected with the optical head unit 100 and each part of the spectroscope 200. Specifically, the control unit 300 is connected with the infrared CCD 142 in the optical head unit 100 to enable generating an observation image of the anterior ocular segment Ea of the subject's eye E. The control unit 300 is also connected with the APD 115 in the optical head unit 100 to enable generating a fundus observation image of the fundus Er of the subject's eye E. Further, the control unit 300 is also connected with the head driving unit 140 in the optical head unit 100 to enable three-dimensionally driving the optical head unit 100 with respect to the subject's eye E.

On the other hand, the control unit 300 is connected also with the line sensor 204 of the spectroscope 200. The spectroscope 200 enables acquiring measurement signals for respective wavelengths, and further generating a tomographic image of the subject's eye E based on these measurement signals.

The generated anterior ocular segment observation image, fundus observation image, and tomographic image of the subject's eye E can be displayed on a monitor 301 connected to the control unit 300.

(Subject's Eye E Alignment Method)

Figure 2:
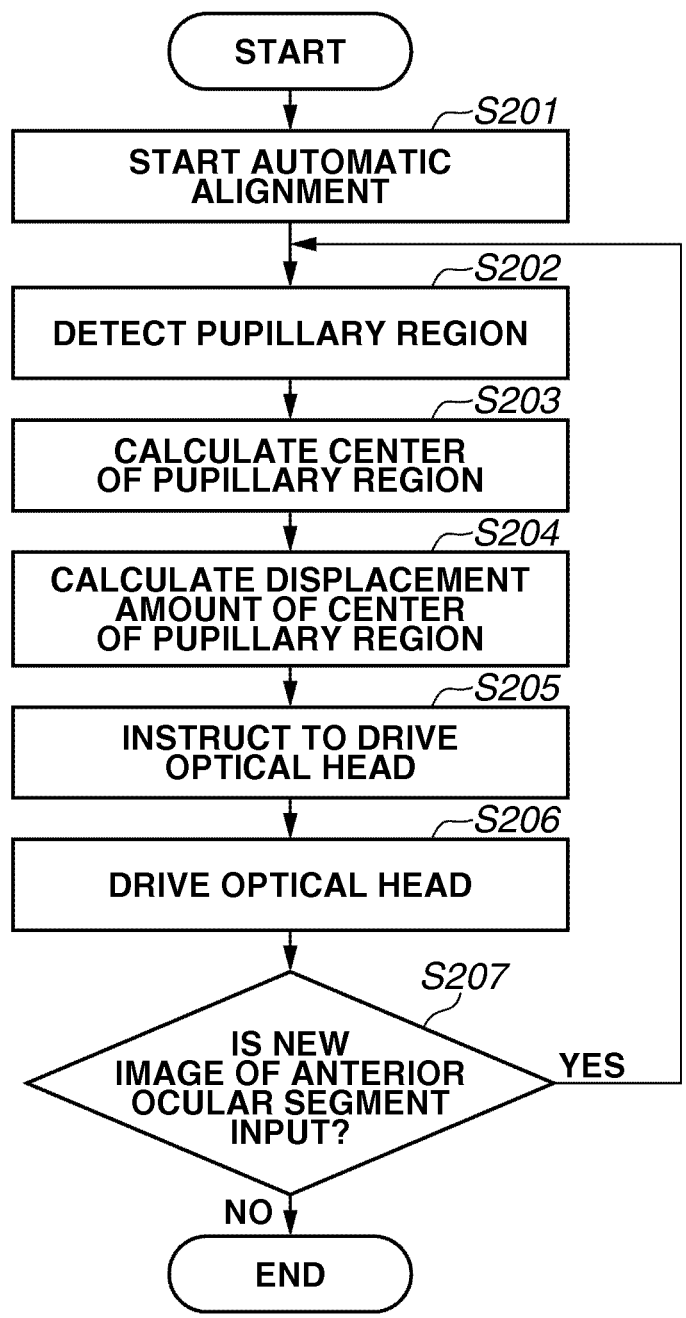
FIG. 2 is a flowchart illustrating an example of automatic alignment according to the first exemplary embodiment.

The following describes a subject's eye E alignment method using the optical coherence tomographic imaging apparatus according to the present exemplary embodiment, with reference to the flowchart illustrated in FIG. 2. Prior to image capturing, an inspector makes a subject sit down in front of the apparatus.

In step S201, upon reception of a switch operation (not illustrated) by the inspector, the control unit 300 starts automatic alignment. In step S202, the control unit 300 functions as an anterior ocular segment image acquisition unit. When automatic alignment is started, the control unit 300 periodically acquires an anterior ocular segment image from the infrared CCD 142, and analyzes it. Specifically, the control unit 300 detects a pupillary region in the input anterior ocular segment image.

In step S203, the control unit 300 calculates the center position of the detected pupillary region. In step S204, the control unit 300 functions as a displacement amount calculation unit, and calculates the amount of displacement between the center position of the detected pupillary region and the center position of the anterior ocular segment image. The optical coherence tomographic imaging apparatus according to the present exemplary embodiment is configured so that the center of the anterior ocular segment image coincides with the optical axis of the objective lens 101-1. The amount of displacement calculated in step S204 represents the amount of displacement between the subject's eye E and the measuring light axis.

In step S205, the control unit 300 instructs the head driving unit 140 to move the optical head unit 100 according to the amount of displacement calculated in step S204. In step S206, the head driving unit 140 drives three motors (not illustrated) to move the position of the optical head unit 100 in the three-dimensional (X, Y, Z) directions with respect to the subject's eye E. As a result of this movement, the position of the optical axis of the objective lens 101-1 mounted on the optical head unit 100 is corrected so as to come close to the pupillary center position of the anterior ocular segment Ea of the subject's eye E.

In step S207, after the movement of the optical head unit 100, the control unit 300 determines whether a new anterior ocular segment image is input from the infrared CCD 142. In a case a new anterior ocular segment image is determined to have been input (YES in step S207), the processing returns to step S202. On the other hand, in a case where a new anterior ocular segment image is determined to have not been input (NO in step S207), the processing exits this flowchart.

With this series of automatic alignments, the optical axis position of the objective lens 101-1 constantly moves so as to constantly track the pupillary center position of the anterior ocular segment Ea of the subject's eye E. Even if the direction of the line of sight of the subject's eye E changes, this automatic alignment enables the optical axis of the objective lens 101-1 to track the pupillary center of the anterior ocular segment Ea after the line of sight is changed (anterior ocular segment tracking). Therefore, the fundus Er is irradiated with the measuring light emitted from the measuring light source 130 without being interrupted by the pupil, achieving stable tomographic image capturing.

The control unit 300 continues this series of automatic alignments until deflection of the measuring light on the fundus Er of the subject's eye E is started to record a tomographic image of the fundus Er of the subject's eye E.

Although, in the present exemplary embodiment, the control unit 300 performs automatic alignment of the optical system for the subject's eye E based on an anterior ocular segment image captured by the infrared CCD 142, automatic alignment may be performed by using other techniques. For example, automatic alignment in the three-dimensional (X, Y, Z) directions can be performed by projecting an alignment index onto the anterior ocular segment of the subject's eye E and detecting the reflected light.

(Fundus Tracking Method)

Figure 3:
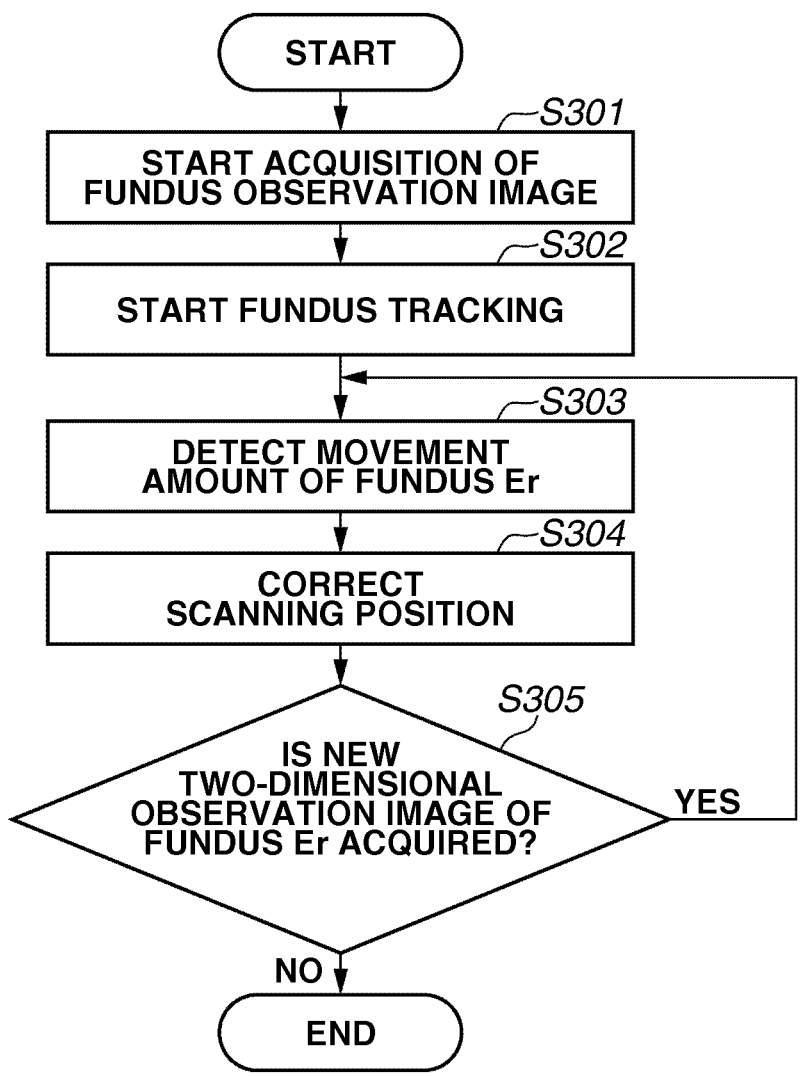
FIG. 3 is a flowchart illustrating an example of fundus tracking according to the first exemplary embodiment.

The following describes a fundus tracking method for correcting the deviation of the measuring light irradiation position due to the subject's eye E movement when irradiating the fundus Er of the subject's eye E with the measuring light to observe the state of the subject's eye E, with reference to the flowchart illustrated in FIG. 3.

In step S301, after the above-described automatic alignment is started, the control unit 300 starts the operation for acquiring a two-dimensional observation image of the fundus Er which has passed through the optical path L2. Specifically, the control unit 300 starts acquiring the reflected light from the fundus Er input from the APD 115. The reflected light from the fundus Er is two-dimensionally and continuously deflected on the fundus Er by the X scanner 117-1 and the Y scanner 117-2. Therefore, periodically combining the reflected light input from the APD 115 enables periodically acquiring a fundus observation image of the fundus Er.

In step S302, the control unit 300 starts fundus tracking based on the periodically acquired fundus observation image. In step S303, the control unit 300 calculates the amount of fundus Er movement by using two fundus observation images (a previously acquired fundus observation image and the current fundus observation image). Specifically, the control unit 300 calculates the amount of displacement between target regions on the fundus observation images in the two-dimensional (X, Y) directions to calculate the amount of fundus Er movement in the two-dimensional (X, Y) directions. The control unit 300 is an example of a movement amount acquisition unit for acquiring the subject's eye movement based on a plurality of subject's eye E images (for example, a plurality of fundus images) acquired at different times. Further, a target region is the macula of the fundus Er, the optic disc, a blood vessel branch, etc., and may be any desired region on the fundus Er as long as the amount of fundus Er movement can be calculated.

In step S304, according to the calculated amount of fundus Er movement, the control unit 300 controls the X scanner 122-1 and the Y scanner 122-2 to perform scanning position correction so that an identical region on the fundus Er is constantly irradiated with the measuring light that takes the optical path L1.

In step 305, the control unit 300 determines whether a new two-dimensional observation image of the fundus Er has been acquired. In a case the new two-dimensional observation image of the fundus Er is determined to have been acquired (YES in step S305), the processing returns to step S303. On the other hand, in a case the new two-dimensional observation image of the fundus Er is determined to have not been acquired (NO in step S305), the processing exits this flowchart.

With this series of fundus tracking, the measuring light radiated from the measuring light source 130 onto the fundus Er moves so as to constantly track the movement of the fundus Er of the subject's eye E, achieving stable tomographic image capturing. The control unit 300 continues this series of fundus tracking until the inspection of the subject's eye E is completed.

Although, in the present exemplary embodiment, the control unit 300 performs fundus tracking by using fundus observation images based on a spot scanning laser ophthalmoscope (SLO), fundus tracking may be performed by using other techniques. For example, the control unit 300 can perform fundus tracking by using two-dimensional fundus observation images acquired through the combination of the infrared light which can be broadly radiated onto the fundus and an infrared CCD. Fundus tracking can also be performed by projecting any desired pattern formed by a light source onto the fundus Er, and detecting the reflected light.

(Tomographic Image Capturing Method)

The following describes a tomographic image capturing method using the optical coherence tomographic imaging apparatus according to the present exemplary embodiment.

The inspector operates a switch (not illustrated) on the control unit 300 to start image capturing. In response to an instruction for starting image capturing, the control unit 300 starts the generation of a tomographic image which is to be recorded, based on the interference light periodically output from the line sensor 204.

The interference light output from the line sensor 204 is a signal for each frequency subjected to spectral diffraction by the diffraction grating 202. The control unit 300 performs the fast Fourier transform (FFT) processing on the signal of the line sensor 204 to generate information in the depth direction at a certain point on the fundus Er. The generation of information in the depth direction at the certain point on this fundus Er is referred to as A scan.

The control unit 300 drives at least either one of the X scanner 122-1 and the Y scanner 122-2 to irradiate the fundus Er with the measuring light, thus the fundus Er can be arbitrarily scanned. The X scanner 122-1 and the Y scanner 122-2 enable deflecting the measuring light on the subject's eye E for scanning.

The control unit 300 combines a plurality of A scans acquired during a scan on an arbitrary locus into a two-dimensional image to generate a tomographic image of the fundus Er on an arbitrary locus.

Further, the control unit 300 drives at least either one of the X scanner 122-1 and the Y scanner 122-2 to repeat the above-described scan on an arbitrary locus a plurality of times. Performing the same locus operation a plurality of times enables acquiring a plurality of tomographic images on an arbitrary locus on the fundus Er. For example, the control unit 300 drives only the X scanner 122-1 to repetitively perform scan in the X direction to generate a plurality of tomographic images on the same scanning line of the fundus Er. Further, the control unit 300 can simultaneously drive the X scanner 122-1 and the Y scanner 122-2 to repetitively perform a circular operation to generate a plurality of tomographic images on an identical circle of the fundus Er. The control unit 300 performs the addition average on the plurality of tomographic images to generate one high-definition tomographic image, and displays it on the monitor 301.

On the other hand, the control unit 300 can drive at least either one of the X scanner 122-1 and the Y scanner 122-2 to perform scanning a plurality of times while shifting each scan on an arbitrary locus in the X and Y directions. For example, the control unit 300 performs scanning in the X direction a plurality of times while shifting each scan at regular intervals in the Y direction to generate a plurality of tomographic images covering the entire rectangular region on the fundus Er. Then, the control unit 300 combines the plurality of tomographic images to generate three-dimensional information of the fundus Er, and displays the information on the monitor 301.

These scanning patterns by the X scanner 122-1 and the Y scanner 122-2 can be arbitrarily switched by pressing a scanning pattern selection button (not illustrated).

(Automatic Alignment Control During Tomographic Image Capturing)

In a case performing scanning a plurality of times as described above to capture a plurality of tomographic images, the time required to perform scanning a plurality of times is longer than the time required to perform a scanning. For example, in the optical coherence tomographic imaging apparatus according to the present exemplary embodiment, the control unit 300 is able to repeat 128 times a 10-mm scan in the X direction on the fundus Er while shifting each scan by 0.078 millimeters in the Y direction. These 128 scans enable acquiring 128 tomographic images and generating three-dimensional information for a 10 mm×10 mm range on the fundus Er. In the optical coherence tomographic imaging apparatus according to the present exemplary embodiment, one tomographic image is composed of a total of 1024 A scans. Each A scan takes 14.3 microseconds. Therefore, since the acquisition of one tomographic image takes 1024×14.3 microseconds=14.6 milliseconds, the acquisition of all of the 128 tomographic images takes at least 14.6 milliseconds× 128=1.87 seconds.

Human eye movements can be roughly classified into three different types: saccade, drift, and tremolo. These eye movements are kinds of involuntary movement, and are difficult to completely stop even if the subject gazes at a fixation lamp. The generation interval of these eye movements is shorter than the above-described image capturing interval (1.87 seconds). In many cases, these eye movements occur a plurality of times during execution of all of 128 scans.

Figure 4:
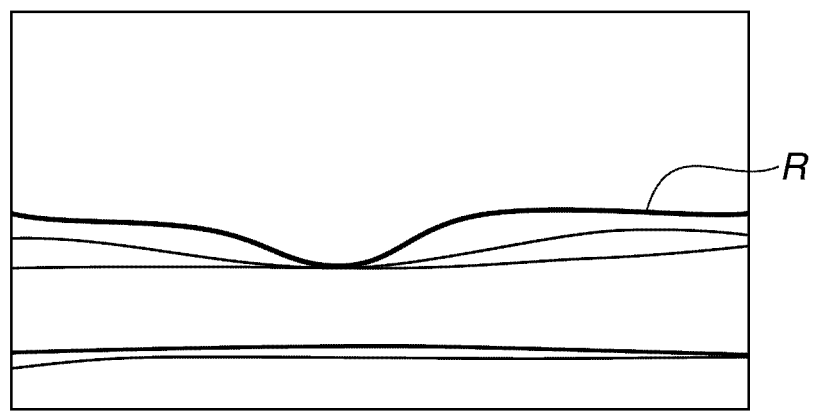
FIG. 4 illustrates an example of a tomographic image captured under suitable alignment conditions according to the first exemplary embodiment.
Figure 5:
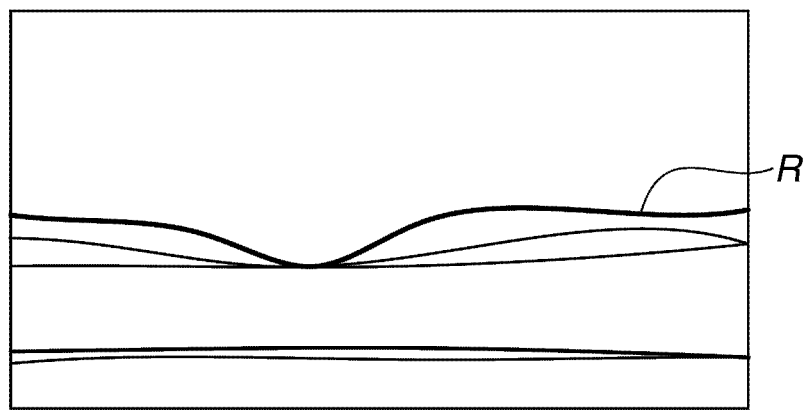
FIG. 5 illustrates an example of a tomographic image captured when an eye is moving according to the first exemplary embodiment.

However, changes in the pupillary position due to these eye movements do not largely affect captured tomographic images. FIG. 4 illustrate an example of a tomographic image captured in a state where the pupillary center of the anterior ocular segment Ea of the subject's eye E coincides with the optical axis of the objective lens 101-1. On the other hand, FIG. 5 illustrate an example of a tomographic image captured in a state where the pupillary center is deviated by about 1 millimeter in the X direction with respect to the optical axis of the objective lens 101-1. In the tomographic image of the fundus Er illustrated in FIG. 5, a retina R is deviated in the X direction in comparison with the tomographic image illustrated in FIG. 4. However, the tomographic image itself has not largely changed in shape. This kind of deviation in the X direction can be corrected by the above-described fundus tracking.

Figure 6:
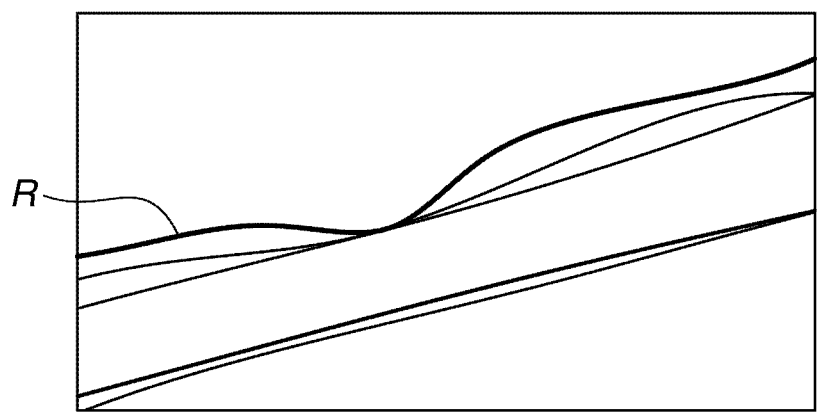
FIG. 6 illustrates an example of a tomographic image captured during execution of automatic alignment according to the first exemplary embodiment.

On the other hand, in a case automatic alignment is activated accompanying the eye movement, the eye movement largely affects a captured tomographic image. FIG. 6 illustrates an example of a tomographic image captured in the state illustrated in FIG. 5 except that automatic alignment is activated so that the pupillary center coincides with the optical axis of the objective lens 101-1. In comparison with the tomographic image illustrated in FIG. 4, a deviation in the X direction arises and further the retina R is largely inclined.

Figure 7:
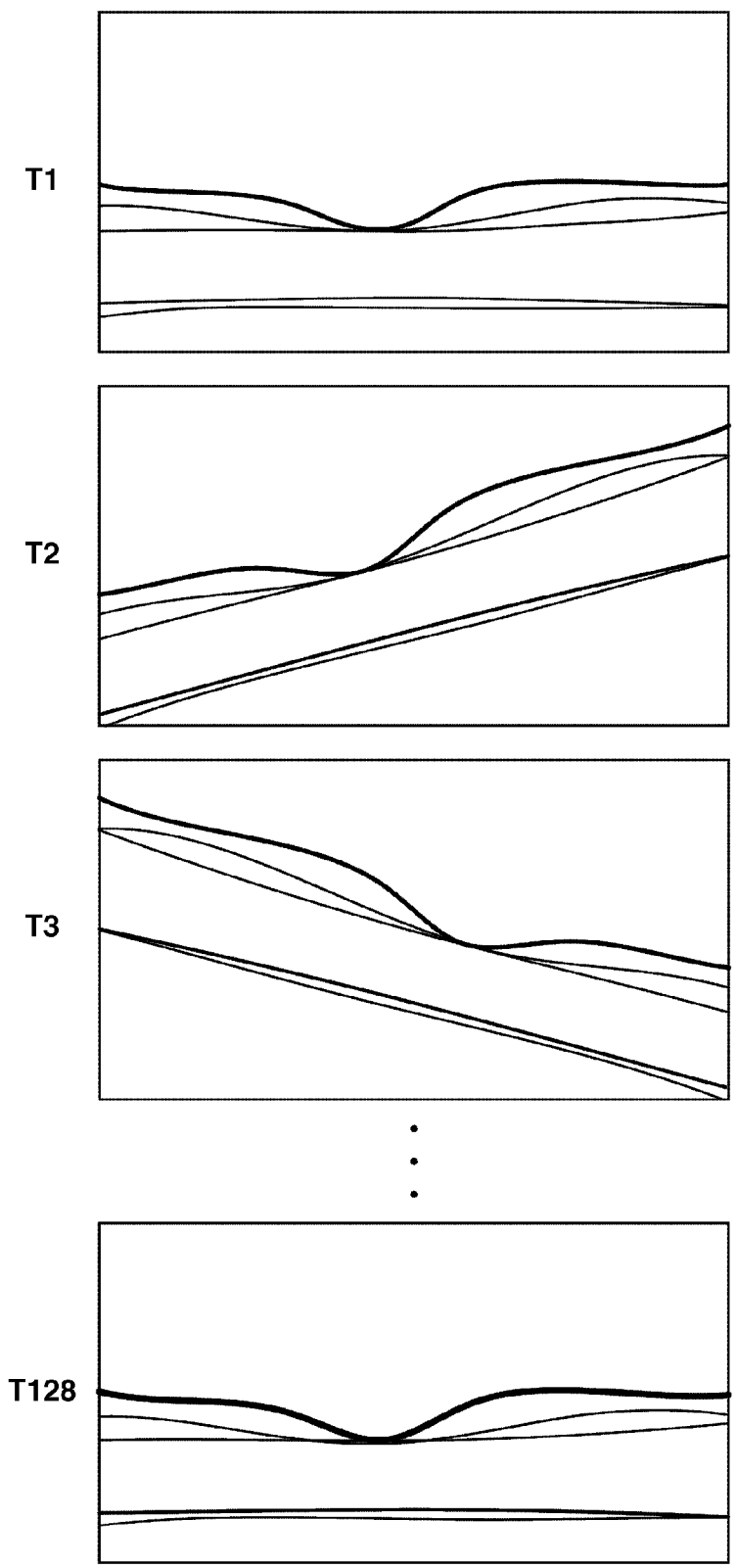
FIG. 7 illustrates examples of a plurality of tomographic images captured during execution of automatic alignment according to the first exemplary embodiment.
Figure 8:
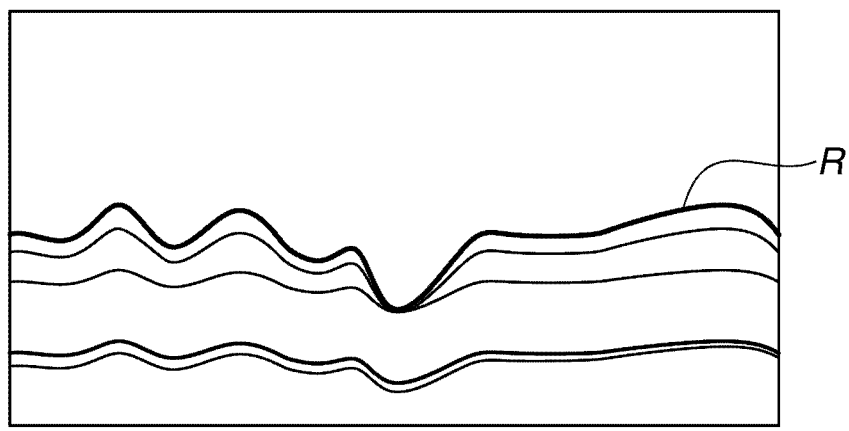
FIG. 8 illustrates an example of a virtual tomographic image generated from a plurality of tomographic images according to the first exemplary embodiment.

This kind of inclination of the retina R cannot be corrected by fundus tracking. In a case automatic alignment is activated while all of 128 scans are being carried out, the inclination of the retina R will largely change in the middle of acquiring 128 tomographic images, as illustrated in FIG. 7. Such changes in the inclination of the retina R produce a noticeable problem particularly in a three-dimensional image which is generated by reconfiguring a plurality of tomographic images. FIG. 8 illustrates an example display of a virtual tomographic image perpendicularly intersecting with the main scanning direction, generated by reconfiguring the 128 tomographic images illustrated in FIG. 7. In this virtual tomographic image, the retina R has largely changed in shape. For an ophthalmologist who diagnoses eye disease based on the condition of the retina R, changes in the inclination of the retina R not only disturb diagnosis but also lead to misdiagnosis.

Therefore, the optical coherence tomographic imaging apparatus according to the present exemplary embodiment suspends automatic alignment during execution of scans for capturing a plurality of tomographic images. This operation will be described below with reference to the flowchart illustrated in FIG. 9. Prior to image capturing, the inspector makes the subject sit down in front of the apparatus. The control unit 300 drives at least either one of the X scanner 122-1 and the Y scanner 122-2 as a scanning unit to switch between observation scan for capturing a tomographic image (hereinafter referred to as a tomographic image for observation) for subject's eye observation and recording scan for capturing a tomographic image (hereinafter referred to as a tomographic image for recording) for subject's eye state recording.

In step S901, upon reception of a switch operation (not illustrated) by the inspector, the control unit 300 starts automatic alignment. In step S902, to observe alignment conditions, the control unit 300 starts capturing an observation tomographic image of the fundus Er.

In step S903, the control unit 300 displays the acquired observation tomographic image on the monitor 301. The inspector can determine right and wrong of alignment conditions with reference to the observation tomographic image displayed on the monitor 301. In a case the inspector determines that alignment conditions are right, the inspector operates a switch (not illustrated) on the control unit 300 to instruct to start tomographic image capturing.

In step S904, in response to a switch operation (not illustrated) by the inspector, the control unit 300 starts capturing tomographic images for recording. In step S905, upon reception of an image capturing start instruction, the control unit 300 suspends automatic alignment before starting image capturing for recording.

In step S906, the control unit 300 starts scanning for generating a plurality of tomographic images for recording. Specifically, the control unit 300 controls at least either one of the X scanner 122-1 and the Y scanner 122-2 to perform scanning on an arbitrary locus a plurality of times.

In step S907, upon completion of all scans, the control unit 300 restarts automatic alignment. In step S908, the control unit 300 generates a plurality of tomographic images corresponding to the plurality of scans. In step S909, the control unit 300 records the plurality of tomographic images generated in step S908 in a recording medium (not illustrated). This completes the processing of the flowchart illustrated in FIG. 9.

Although, in the present exemplary embodiment, automatic alignment is suspended immediately before starting scans for acquiring tomographic images for recording, automatic alignment may be suspended before that timing. Specifically, automatic alignment may be suspended when the pupillary position of the subject's eye E is determined to almost coincide with the optical axis of the optical system through automatic alignment.

Further, a reception unit for receiving a signal for acquiring a plurality of tomographic images may be provided, and the processing for tomographic image acquisition may be started after reception of the signal.

As described above, in the optical coherence tomographic imaging apparatus according to the present exemplary embodiment, the control unit 300 suspends automatic alignment at least when generating tomographic images for recording, enabling acquiring suitable tomographic images having less distortion.

(Fundus Tracking Control During Tomographic Image Capturing)

Also in a case fundus tracking is performed during scan for acquiring one tomographic image, the captured tomographic image is largely affected. As described above, in the optical coherence tomographic imaging apparatus according to the present exemplary embodiment, the acquisition of one tomographic image takes 14.6 milliseconds. Therefore, in a case acquiring a plurality of tomographic images, the control unit 300 scans the fundus Er a plurality of times with a period of about 14.6 milliseconds. This interval depends on the number of A scans required to form one tomographic image, and on the time required to acquire one A scan. On the other hand, in the optical coherence tomographic imaging apparatus according to the present exemplary embodiment, the period of scanning position correction through fundus tracking is 33.3 milliseconds. This period depends on the acquisition interval of fundus observation images of the fundus Er which is used to calculate the amount of displacement for scanning position correction.

Figure 10:
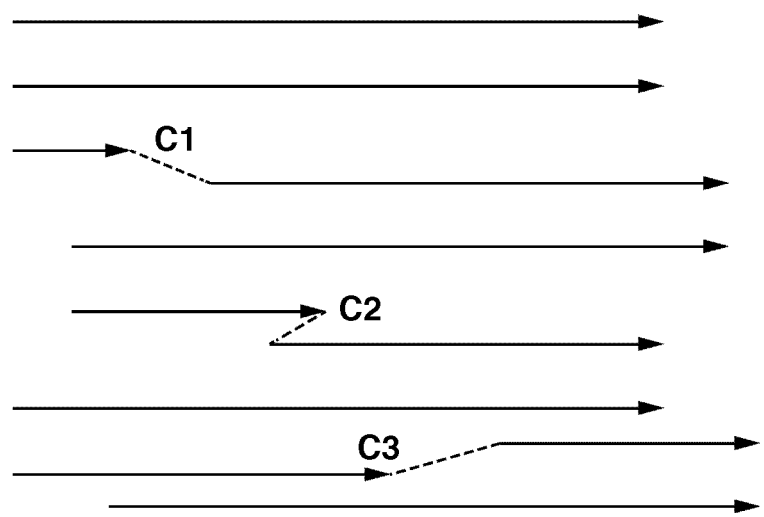
FIG. 10 illustrates an example of a scanning pattern without fundus tracking control according to the first exemplary embodiment.
Figure 11:
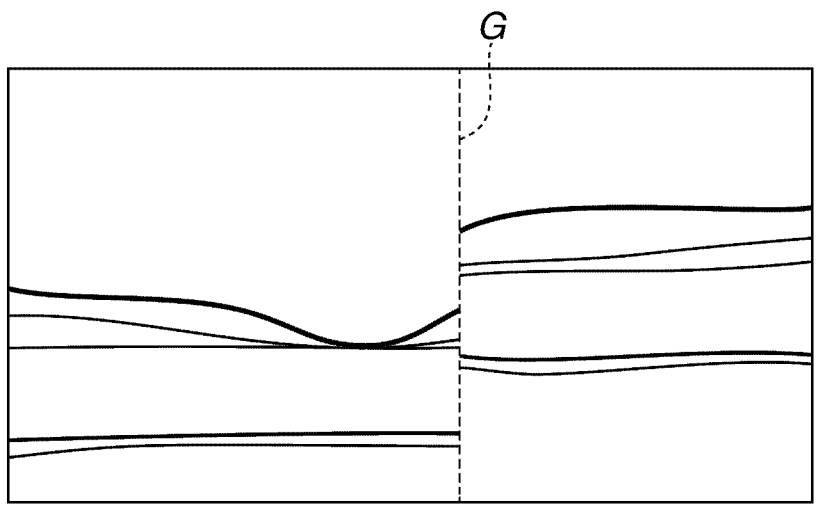
FIG. 11 illustrates an example of a tomographic image acquired through scanning according to the first exemplary embodiment.

Thus, in a case the acquisition interval of tomographic images differs from the acquisition interval of fundus observation images, the control unit 300 performs scanning position correction at timings Ci (i=1 to 3) through fundus tracking during the scan of the fundus Er to acquire one tomographic image, as illustrated in FIG. 10. Although, in fundus tracking, the scanning position correction is performed at long intervals, actual correction is performed at very high speed. Therefore, the operation of fundus tracking is performed in such a way that scanning position correction is instantaneously carried out in response to all of eye movements occurring within the correction intervals. Therefore, in a case scanning position correction through fundus tracking is performed during the scan on the fundus Er to acquire one tomographic image, a gap G of the retina layer will appear, as illustrated in FIG. 11. For an ophthalmologist who diagnoses eye disease based on the shape of the retina layer, the gap G of the retina layer not only disturbs diagnosis but also leads to misdiagnosis.

In the optical coherence tomographic imaging apparatus according to the present exemplary embodiment, when capturing a plurality of tomographic images, the control unit 300 performs scanning position correction through fundus tracking between scans for each tomographic image acquisition, and suspends the scanning position correction during scan. This operation will be described below with reference to the flowchart illustrated in FIG. 12. Prior to image capturing, the inspector makes the subject sit down in front of the apparatus. The control unit 300 can drive at least either one of the X scanner 122-1 and the Y scanner 122-2 as a scanning unit to switch between observation scan for capturing a tomographic image for subject's eye observation and recording scan for capturing a tomographic image for subject's eye state recording.

In step S1201, upon reception of a switch operation (not illustrated) by the inspector, the control unit 300 starts automatic alignment. Then, to observe alignment conditions, the control unit 300 starts capturing an observation tomographic image of the fundus Er. In step S1202, the control unit 300 displays the acquired observation tomographic image on the monitor 301. The inspector can determine right or wrong of alignment conditions with reference to the observation tomographic image displayed on the monitor 301.

In step S1203, the inspector determines that alignment conditions are right, and, upon reception of a switch operation (not illustrated), the control unit 300 starts capturing tomographic images for recording. In steps S1201 to S1203, to adjust a coherence gate, the control unit 300 may perform scanning position correction based on fundus tracking.

In step S1204, the control unit 300 drives at least either one of the X scanner 122-1 and the Y scanner 122-2 as a scanning unit to start a scan on an arbitrary locus.

In step S1205, the control unit 300 functions as a fundus image acquisition unit, and determines whether a captured fundus image has been acquired. In a case it is determined that a fundus image has been acquired (YES in step S1205), the processing proceeds to step S1206. On the other hand, in a case it is determined that a fundus image has not been acquired (NO in step S1205), the processing proceeds to step S1208.

In step S1206, the control unit 300 functions as a movement amount calculation unit, and calculates the amount of fundus Er movement based on fundus images already acquired and newly acquired.

In step S1207, the control unit 300 stores in memory (not illustrated) information indicating that the fundus Er movement was detected during a scan, and information indicating the amount of the detected fundus Er movement. Then, the processing proceeds to step S1208. In step S1208, the control unit 300 ends a scan.

In step S1209, based on the information stored in memory (not illustrated), the control unit 300 determines whether the fundus Er movement has been detected during execution of a scan. In a case it is determined that the fundus Er movement has been detected (YES in step S1209), the processing proceeds to step S1210. On the other hand, in a case it is determined that the fundus Er movement has not been detected (NO in step S1209), the processing proceeds to step S1212.

In step S1210, the control unit 300 reads the calculated amount of fundus Er movement from memory (not illustrated). In step S1211, the control unit 300 calculates the next scanning starting position corrected by offsetting the amount of fundus Er movement, and moves the next scanning position to the offset scanning starting position.

In step S1212, the control unit 300 drives at least either one of the X scanner 122-1 and the Y scanner 122-2 as a scanning unit to move the scanning position to the next scanning starting position.

In step S1213, the control unit 300 determines whether a series of scans is completed. In a case a series of scans is determined to be completed (YES in step S1213), the processing proceeds to step S1214. On the other hand, in a case it is determined that the next scan has not been performed (NO in step S1213), the processing returns to step S1204. In step S1204, the control unit 300 repeats a series of fundus tracking.

In step S1214, the control unit 300 generates a plurality of tomographic images for recording corresponding to a series of a plurality of scans. In step S1215, the control unit 300 displays the plurality of tomographic images for recording generated in step S1214 on the monitor 301. This completes the processing of the flowchart illustrated in FIG. 12. Thus, the control unit 300 suspends the scanning position correction during a scan, and performs scanning position correction between a scan and the next scan. The control unit 300 may control the scanning unit to perform the scanning position correction during sub scan by the scanning unit, and to suspend the scanning position correction during main scan by the scanning unit.

Figure 12:
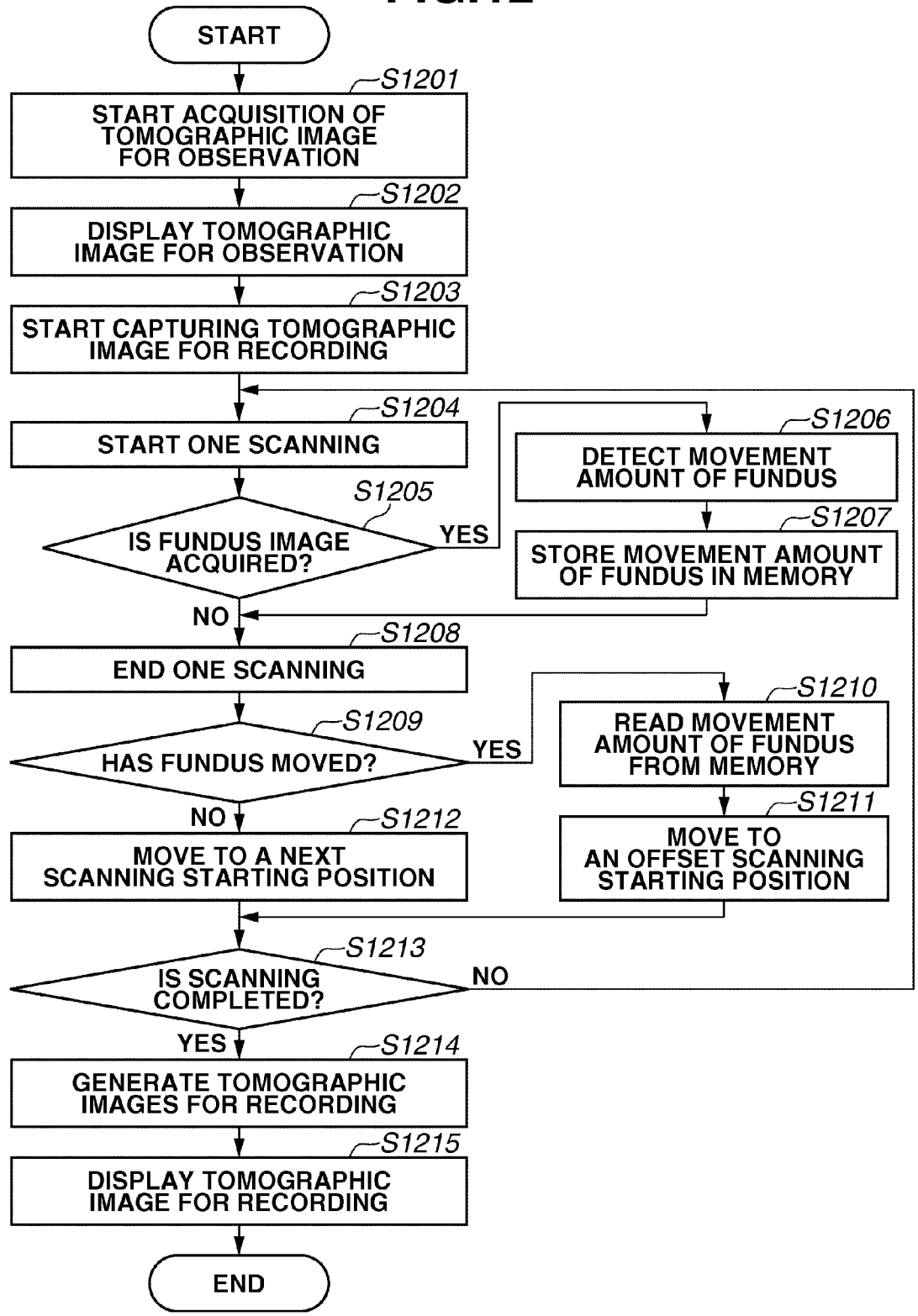
FIG. 12 is a flowchart illustrating an example of fundus tracking control according to the first exemplary embodiment.
Figure 13:
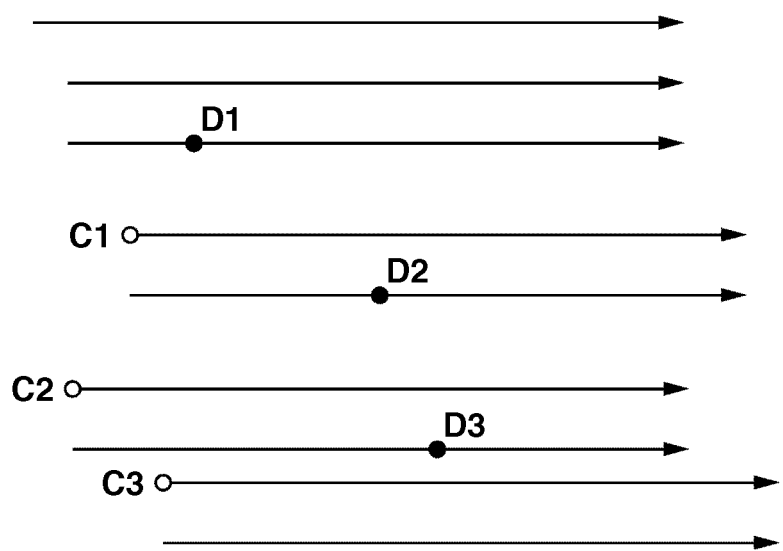
FIG. 13 illustrates an example of a scanning pattern in fundus tracking control according to the first exemplary embodiment.

The following describes an example of scanning in which the control unit 300 scans the fundus Er a plurality of times while performing fundus tracking according to the flowchart illustrated in FIG. 12, with reference to FIG. 13. The fundus Er movement is detected at timings Di (i=1 to 3), and scanning position correction is performed based on the calculated amount of movement at timings Ci (i=1 to 3). As illustrated in FIG. 13, the scanning position correction accompanying the fundus Er movement detected at the timing D1 is delayed till the next scan is started at the timing C1. Similarly, the scanning position correction accompanying the fundus Er movement detected at timings D2 and D3 is delayed till timings C2 and C3, respectively. Performing control in this way enables completely and continuously scanning the fundus Er of the subject's eye E without interruption. Therefore, it is possible to reduce the possibility that the gap G of the retina layer as illustrated in FIG. 11 appears on a captured tomographic image for recording. As for the tomographic images acquired by scans at the timings D1, D2, and D3 at which the fundus Er movement was detected, the scanning position is not corrected, and therefore the possibility that the gap G of the retina layer appears is low. However, since the fundus Er moves during scan, a distortion may possibly arise in the acquired tomographic image to a certain extent. Therefore, the control unit 300 may remove tomographic images acquired by scans at the timings D1, D2, and D3, or perform again the same scans at respective scanning positions to capture tomographic images again. Thus, tomographic images having less distortion can be acquired.

Figure 9:
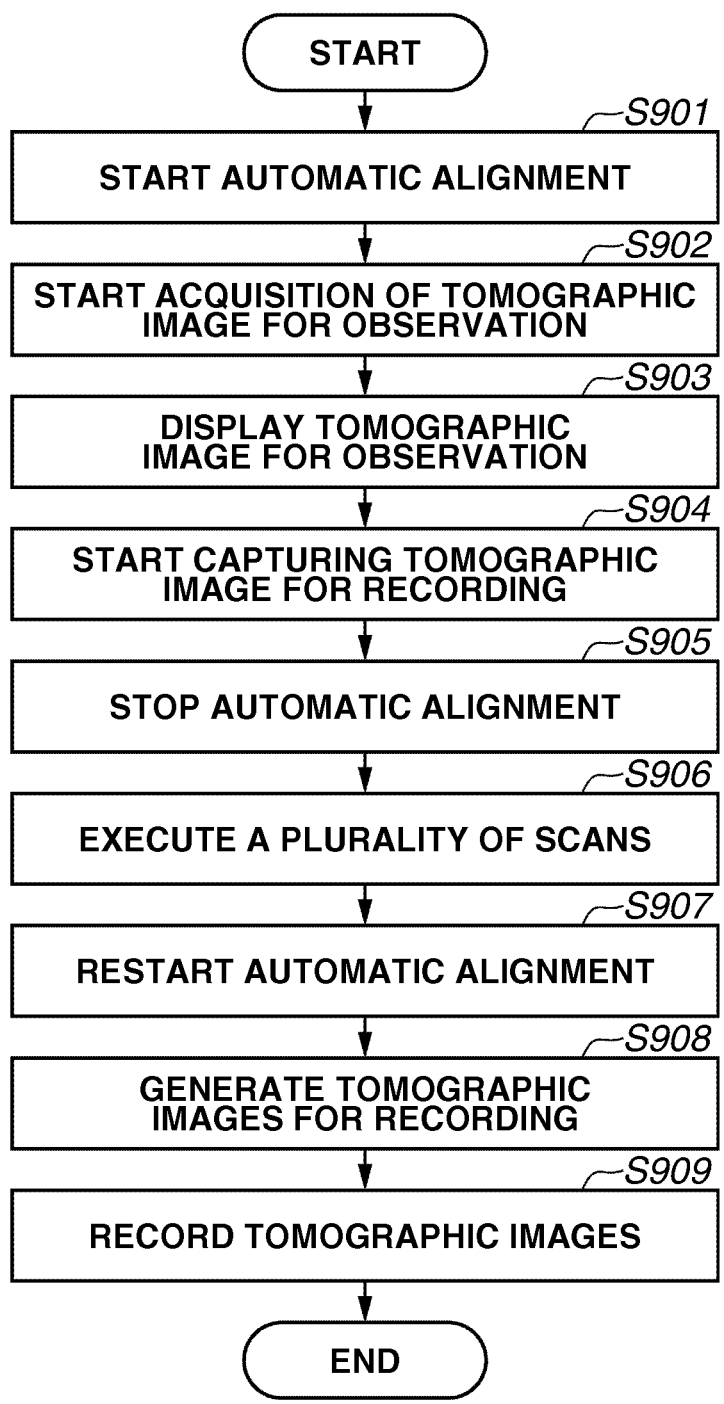
FIG. 9 is a flowchart illustrating an example of automatic alignment control according to the first exemplary embodiment.

In the processing of the flowchart illustrated in FIG. 12, the control unit 300 may parallelly perform the automatic alignment suspending processing and the automatic alignment restart processing in steps S905 and S907, respectively, illustrated in FIG. 9. Specifically, the control unit 300 may perform the alignment suspending processing in step S905 between the processing in step S1203 and the processing in step S1204, and perform the alignment restart processing in step S907 between the processing in step S1213 and the processing in step S1214. Thus, the control unit 300 may perform at least either one of the automatic alignment processing illustrated in FIG. 9 and the scanning position correction processing based on fundus tracking illustrated in FIG. 12.

Although, in the present exemplary embodiment, the control unit 300 performs control to perform scanning position correction between scans (between a scan and the next scan) when acquiring a tomographic image for recording, the control unit 300 may perform similar control also when acquiring a tomographic image for observation. In this case, a distortion of the retina layer can be reduced also in tomographic images for observation. Further, when acquiring a tomographic image for observation, instead of performing scanning position correction between scans (between a scan and the next scan), the control unit 300 may perform scanning position correction when the fundus Er movement is detected. Tomographic images for observation are displayed as a real-time observation moving image, and therefore the display period is very short. Further, tomographic images for observation are not used for diagnosis, and therefore a distortion of the retina layer is permissible to a certain extent.

As described above, in the optical coherence tomographic imaging apparatus according to the present exemplary embodiment, during execution of a scan, the control unit 300 suspends at least either one of the alignment of the optical system relative to the subject's eye for capturing an image of the subject's eye and the scanning position correction through fundus tracking of the subject's eye. Thus, tomographic images having less distortion can be acquired.

(Configuring Fundus Observation Optical System with Apparatus Other than SLO Optical System)

Figure 14A:
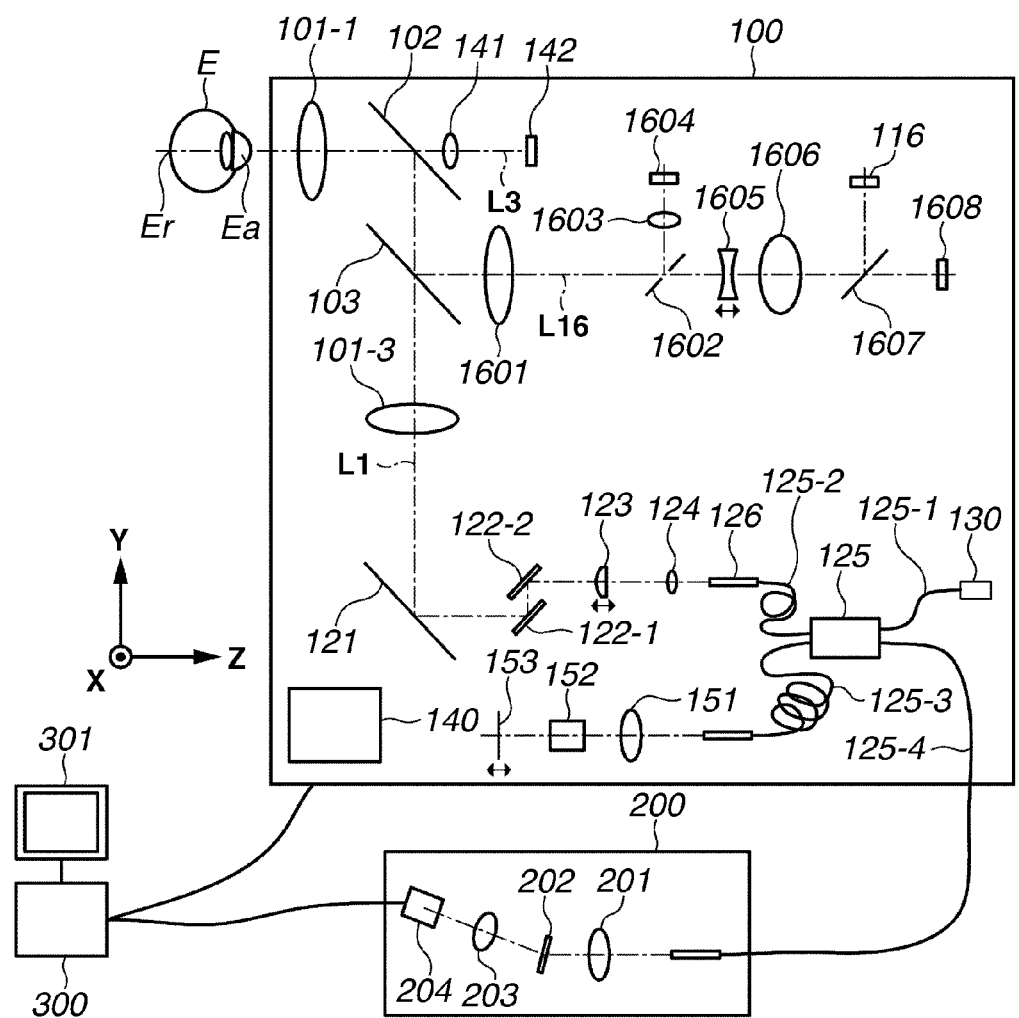
FIGS. 14A and 14B illustrate examples of configurations of an optical coherence tomographic imaging apparatus according to a second exemplary embodiment.
Figure 14B:
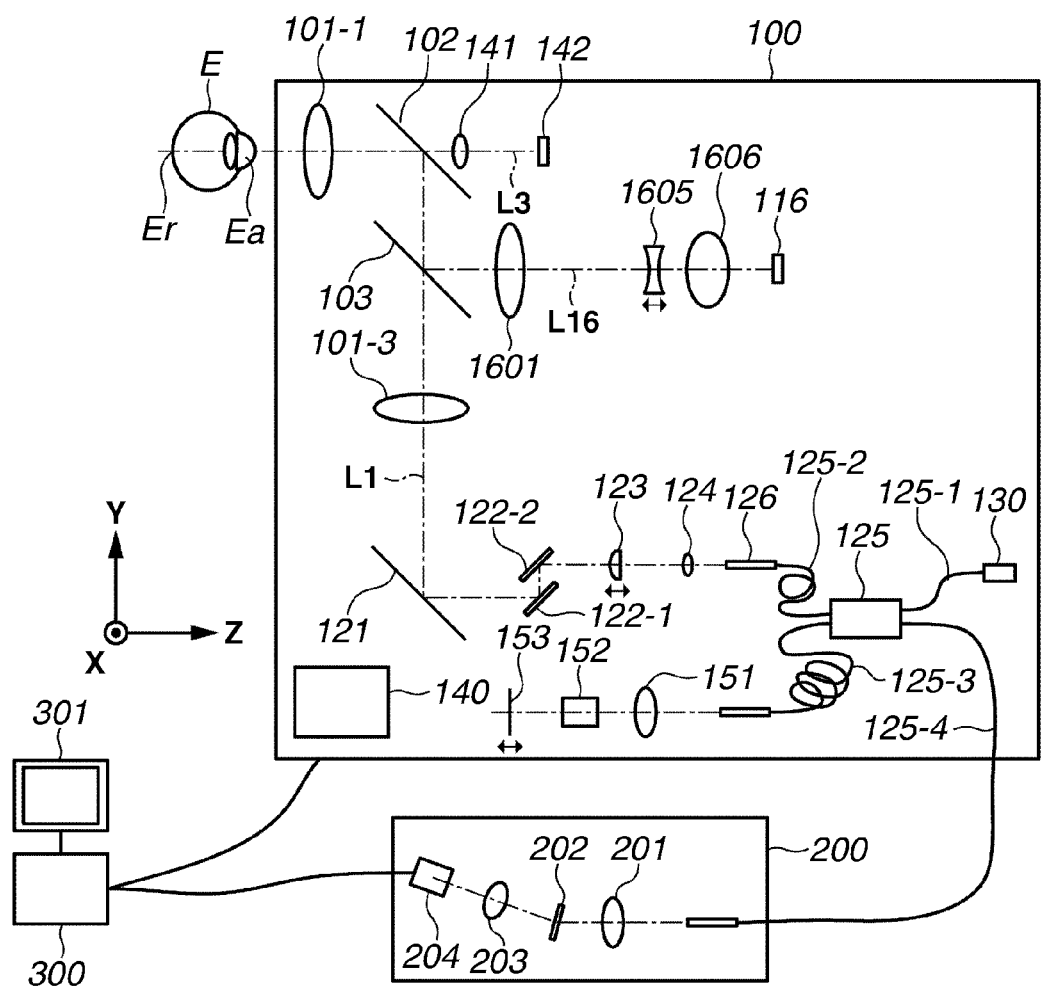

A second exemplary embodiment will be described below with reference to FIGS. 14A and 14B. FIGS. 14A and 14B illustrate examples of configurations of an optical coherence tomographic imaging apparatus according to the second exemplary embodiment. Although the configuration illustrated in FIG. 14A is almost similar to the configuration illustrated in FIG. 1, an optical path L16 is disposed instead of the optical path L2.

The configuration illustrated in FIG. 14A will be described below. The configuration illustrated in FIG. 14A uses a CCD instead of an APD to acquire fundus observation images. A lens 1601, a perforated mirror 1602, lens 1605 and 1606, and a dichroic mirror 1607 are disposed on the optical path L16 in this order. A lens 1603 and a fundus observation light source 1604 are disposed on the reflection side of the perforated mirror 1602. The dichroic mirror 1607 transmits a wavelength in the vicinity of the fundus observation light source 1604, specifically, 780 nanometers. A fundus observation CCD 1608 is disposed on the penetration side, and a fixation lamp light source 116 is disposed on the reflection side. The lens 1605 is driven by a motor (not illustrated) for focusing adjustment for the fixation lamp and fundus observation. The CCD 1608 has sensitivity in the vicinity of the wavelength of the fundus observation light source 1604.

Fundus images acquired by the CCD 1508 can be handled in a similar way to fundus images in the first exemplary embodiment. Therefore, the control unit 300 controls fundus tracking, detection of the amount of movement, and the scanning position correction in a similar way to the first exemplary embodiment. Although, in the present exemplary embodiment, a CCD is used, a CMOS or other two-dimensional sensors may be used.

The configuration illustrated in FIG. 14B will be described below. The configuration illustrated in FIG. 14B is similar to the configuration illustrated in FIG. 14A except that a dedicated fundus observation light source, a fundus observation sensor, and a related mirror or lens are not provided. Similar to the first exemplary embodiment, to acquire a fundus observation image, a computer 300 performs the FFT processing on a signal of a licenser 204, and performs control to generate information in the depth direction at a certain point on the fundus Er. In the first exemplary embodiment, this information in the depth direction is used to acquire a tomogram image. In the present exemplary embodiment, this information in the depth direction is accumulated for use as information indicating the state of a certain point on the fundus Er. Similar to the case of tomographic image acquisition in the first exemplary embodiment, the control unit 300 can accumulate the information in the depth direction at each point within a 10-mm range in the X direction, and repeats the relevant processing 128 times to acquire the state of each point within a 10 mm×10 mm range on the fundus Er. By converting the information into density and luminance, an image indicating the state of the fundus within the above-described range can be acquired.

Using this image as a fundus observation image enables scanning position correction between scans in a similar way to the first exemplary embodiment. However, in the present exemplary embodiment, since the control unit 300 needs to control the X scanner 122-1 and the Y scanner 122-2 to acquire a fundus observation image, the control unit 300 cannot perform scan for tomographic image acquisition during fundus observation image acquisition. The control unit 300 needs to perform fundus observation image acquisition between each of the scans. On the other hand, in the present exemplary embodiment, since neither a dedicated fundus observation light source nor a fundus observation sensor is provided, there is an advantage that the cost of the apparatus can be reduced.

(Determining Whether Amount of Subject's Eye Movement Exceeds Threshold Value)

Figure 15:
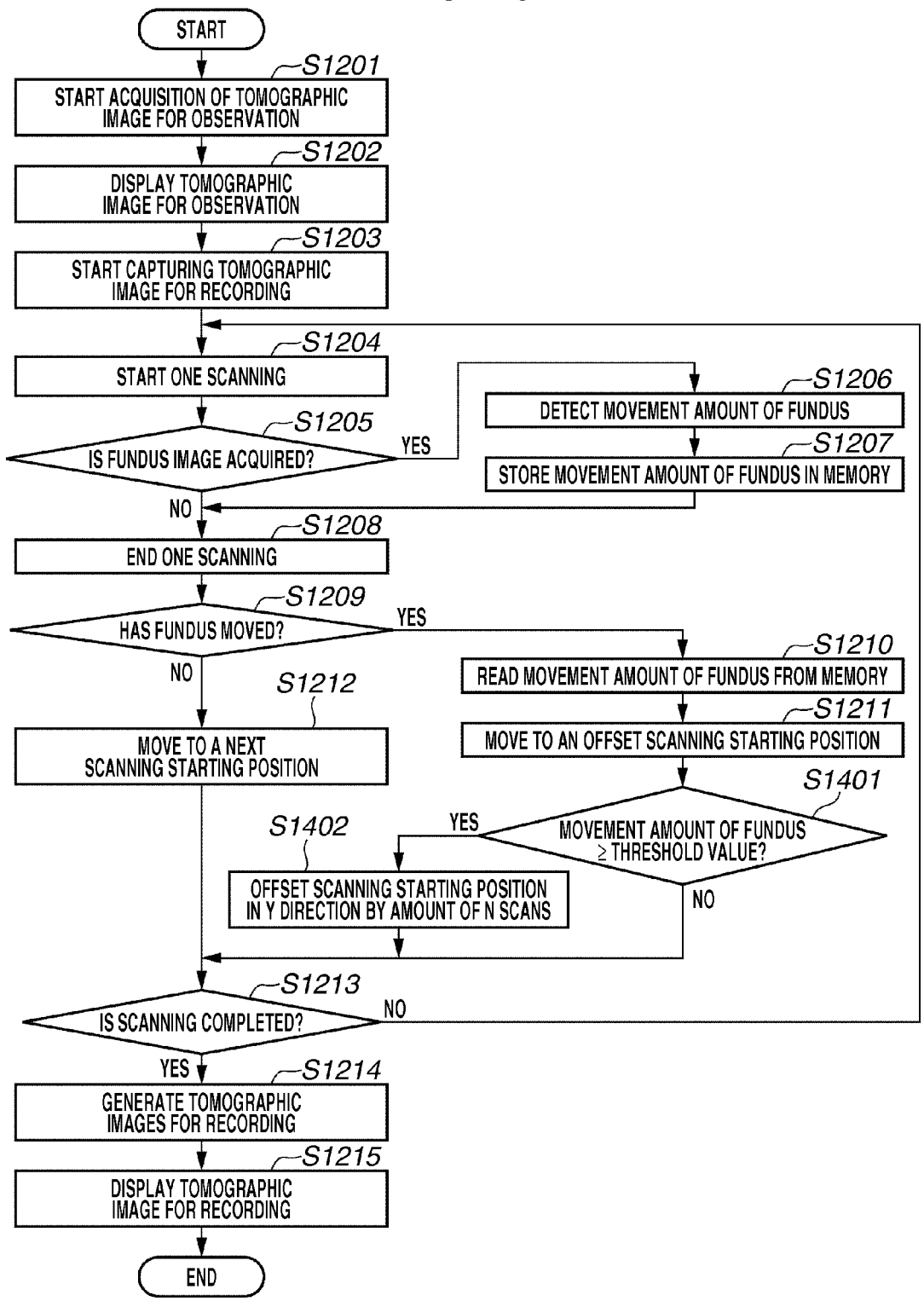
FIG. 15 is a flowchart illustrating an example of fundus tracking control according to a third exemplary embodiment.

FIG. 15 is a flowchart illustrating an example of fundus tracking control according to a third exemplary embodiment. The control unit 300 performs alignment of the subject's eye, fundus tracking, and tomographic image capturing in a similar way to the first exemplary embodiment.

In the present exemplary embodiment, in a case the amount of subject's eye movement before a scan is equal to or smaller than a threshold value, the control unit 300 performs scanning position correction between a scan and the next scan based on the relevant amount of movement. Further, in a case the mount of subject's eye movement before a scan exceeds the threshold value, the control unit 300 restarts scan of the scanning unit from a scanning position before a scan.

In a case performing scanning position correction between a scan and the next scan, if the fundus Er movement is very fast or if the processing speed for scanning is not sufficient, the control unit 300 may not perform scanning position correction in time. Then, a first distortion arises in the tomographic image caused by the fundus Er movement, and then a second distortion arises due to scanning position correction at delayed timing. In this way, the scanning position correction may increase the number of tomographic image distortions. To solve this problem, the control unit 300 restarts scan from a scan before the fundus Er movement occurs. Thus, tomographic images having less distortion can be acquired.

FIG. 15 is a flowchart illustrating processing for restarting scan by the scanning unit. The flowchart illustrated in FIG. 15 is almost identical to the flowchart illustrated in FIG. 12 except that steps S1401 and S1402 are added. Specifically, up to step S1211, the control unit 300 performs scanning position correction in a similar way to the first exemplary embodiment. In step S1401, the control unit 300 as an example of a determination unit determines whether the amount of subject's eye movement before a scan by the scanning unit exceeds a threshold value. This amount of movement refers to the amount of fundus Er movement occurring during N scans. The value of N is an apparatus-specific value and is determined by the frame rate for fundus image acquisition, the frame rate for scan, and the fundus image processing time. In the present exemplary embodiment, N is about 5. The threshold value of the amount of fundus Er movement is determined by the resolution of the apparatus between the scans and the frame rate for fundus image acquisition. In the present exemplary embodiment, the threshold value is about 10 to 100 micrometers. In a case the amount of fundus Er movement is determined to be smaller than the threshold value (NO in step S1401), then in step S1212, the control unit 300 performs processing in subsequent steps in a similar way to the first exemplary embodiment. On the other hand, in a case the amount of fundus Er movement is determined to be equal to or greater than the threshold value (YES in step S1401), then in step S1402, the control unit 300 offsets the scanning starting position. The control unit 300 performs this offsetting of the past N scans in a backward direction. For example, in the present exemplary embodiment, the control unit 300 repeats 128 times a 10-mm scan in the X direction on the fundus Er while shifting each scan by 0.078 millimeters in the Y direction. In this case, the offset is 0.078×N millimeters in the Y direction. In this way, the control unit 300 achieves control for restarting scan from a past scan.

Thus, even if the control unit 300 cannot perform scanning position correction in time, the control unit 300 restarts scan from a scan before a tomographic image distortion occurs. Thus, tomographic images having less distortion can be acquired.

(Detection of Amount of Fundus Rotation)

A fourth exemplary embodiment will be described below. The apparatus configuration according to the present exemplary embodiment is similar to that according to the first exemplary embodiment, and redundant descriptions thereof will be omitted. The control unit 300 performs alignment of the subject's eye, fundus tracking, and tomographic image capturing in a similar way to the first exemplary embodiment.

The present exemplary embodiment differs from the first exemplary embodiment in that it detects the amount of fundus Er rotation in addition to the amount of fundus Er movement. In the first exemplary embodiment, since the control unit 300 detects the amount of fundus Er movement in the X and Y directions to perform scanning position correction, a tomographic image may not provide a straight line on the fundus Er if the angle of the subject's eye E changes during processing. Then, the control unit 300 detects the amount of fundus rotation to correct the rotational direction of scan.

Specifically, the control unit 300 detects the amount of fundus rotation as follows. The control unit 300 sets two target regions on each fundus observation image, and detects respective target regions in the previous fundus observation image and the current fundus observation image. The coordinates of the target regions detected in the previous fundus observation image are A1 (xa1, ya1) and B1 (xb1, yb1), and the coordinates of the target regions detected in the current fundus observation image are A2 (xa2, ya2) and B2 (xb2, yb2). In this case, A2 indicates the same target region as A1, and B2 indicates the same target region as B1.

Generally, the coordinate transformation based on the combination of parallel translation, and rotation in the two-dimensional coordinates are represented by an affine transformation matrix. The control unit 300 performs the coordinate transformation from the coordinates of the previous fundus observation image into the coordinates of the current fundus observation image as follows. First, the control unit 300 performs parallel translation so that the target region A1 coincides with the origin (0, 0). The control unit 300 sets a vector (tx1, ty1) for representing this translation. Then, the control unit 300 performs rotation centering on the origin (=A1) so that a vector A2B2 (xb2-xa2, yb2-ya2) coincides with a vector A1B1 (xb1-xa1, yb1-ya1). This rotation is performed with a rotational angle θ. Finally, the control unit 300 performs translation so that the origin (=A1) coincides with the target region A2. The control unit 300 sets a vector (tx2, ty2) for representing this translation. This translation can be represented by an affine transformation matrix as follows.

$$\begin{pmatrix} x' \\ y' \\ 1 \end{pmatrix} = \begin{pmatrix} 1 & 0 & tx2 \\ 0 & 1 & ty2 \\ 0 & 0 & 1 \end{pmatrix} \begin{pmatrix} \cos\theta & -\sin\theta & 0 \\ \sin\theta & \cos\theta & 0 \\ 0 & 0 & 1 \end{pmatrix} \begin{pmatrix} 1 & 0 & tx1 \\ 0 & 1 & ty1 \\ 0 & 0 & 1 \end{pmatrix} \begin{pmatrix} x \\ y \\ 1 \end{pmatrix}$$ [Formula 1]

(x, y) indicates the coordinates before transformation, and (x', y') indicates the coordinates to be acquired after transformation. The control unit 300 performs coordinate transformation for all of subsequent scans by using this coordinate transformation matrix.

Figure 16:
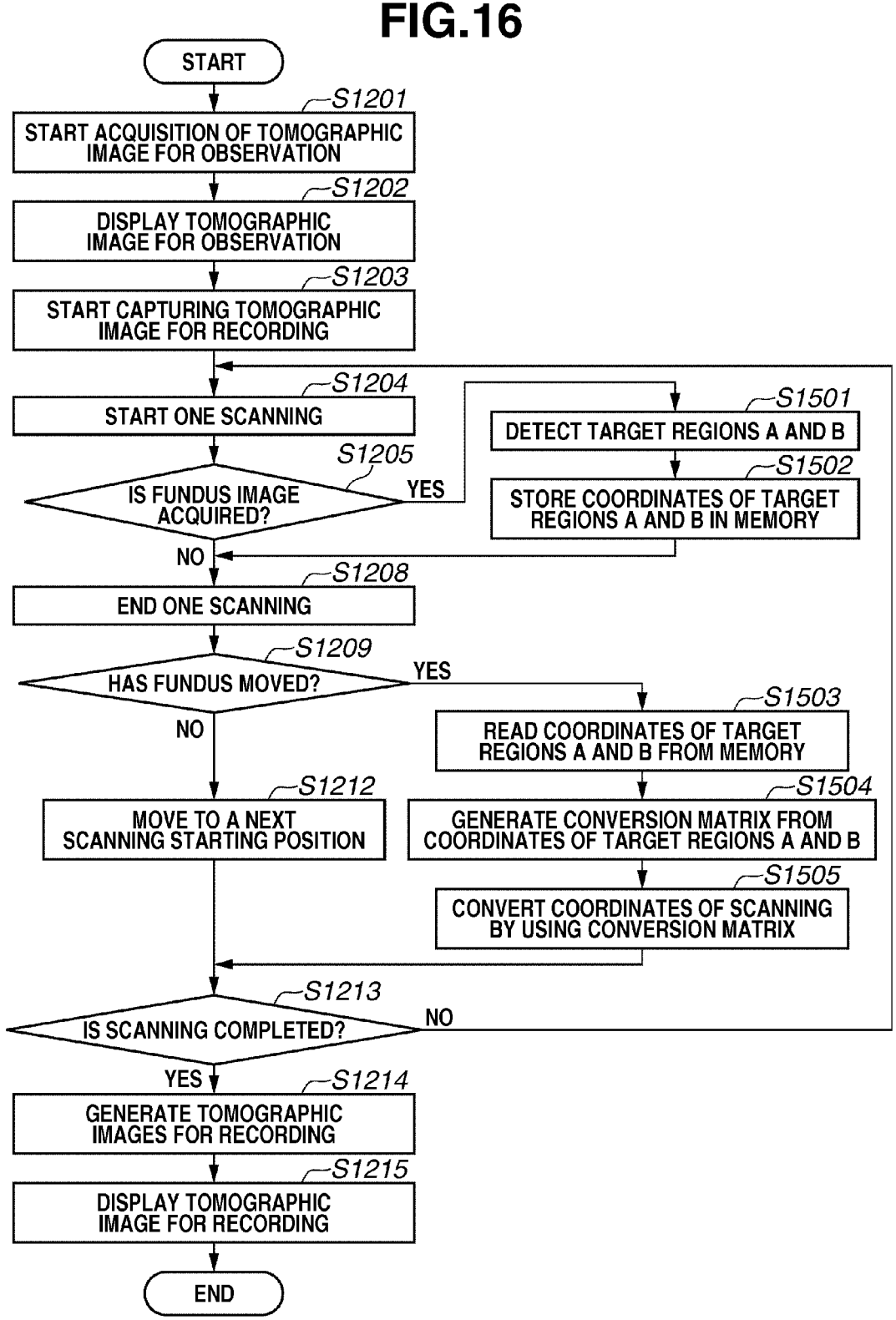
FIG. 16 is a flowchart illustrating an example of fundus tracking control according to a fourth exemplary embodiment.

FIG. 16 illustrates a flowchart to which processing for correcting the amount of fundus rotation is added. Although the flowchart illustrated in FIG. 16 is almost similar to the flowchart illustrated in FIG. 12 except that the control unit 300 generates and applies a coordinate transformation matrix formed through the affine transformation based on the target regions A and B. After a fundus image has been acquired, in step S1501, the control unit 300 detects the target regions A and B. In step 1502, the control unit 300 stores the coordinates of the detected target regions in memory. In step S1503, the control unit 300 reads the coordinates of the target regions A and B from memory. In step S1504, based on the coordinates (A1, B1, A2, B2) of the target regions A and B, the control unit 300 generates a coordinate transformation matrix through the affine transformation. In step 1505, the control unit 300 transforms the coordinates of subsequent scans by using the generated coordinate transformation matrix. Thus, the control unit 300 can continue scanning so that the scan locus forms a straight line on the fundus Er.

(Detection of Subject's Eye Blink)

A fifth exemplary embodiment will be described below. The apparatus configuration according to the present exemplary embodiment is similar to that according to the second exemplary embodiment, and redundant descriptions thereof will be omitted. In the present exemplary embodiment, the control unit 300 detects the amount of fundus Er movement, detects a blink of the subject's eye, and stores and reads coordinates in/from memory according to the flowchart illustrated in FIG. 15. Further, the condition in step S1401 is changed to "amount of fundus movement threshold value, or is a subject's eye blink detected?". Processing for other control is similar to that according to the third exemplary embodiment.

According to the present exemplary embodiment, the control unit 300 determines a blink of the subject's eye as follows. First, the control unit 300 as an example of a detection unit detects the target regions described in the first exemplary embodiment in a plurality of fundus observation images acquired in succession. In a case the detection of the target region fails once or a plurality of times in succession, and then the detection of the same target region is successfully completed once or a plurality of times in succession, the control unit 300 determines that the subject's eye Er has blinked. The upper and the lower limits of the number of times of successive success or failure are apparatus-specific values which are determined by comparing the frame rate for fundus observation image acquisition with the blinking time of a healthy eye.

With the above-described control, in a case the subject's eye Er blinks, the control unit 300 can return to a scan before the blink and then restart scan. Therefore, even if a blink causes information loss and suitable tomographic image acquisition fails, the above-described control enables acquiring of suitable tomographic images without information loss. In addition to the detection using the target region, the control unit 300 may detects a blink by using anterior ocular segment images for the subject's eye. For example, the control unit 300 may determine the detection of a blink in a case the area of the pupillary region in the anterior ocular segment image is smaller than a threshold value.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-017661 filed Jan. 31, 2013, which is hereby incorporated by reference herein in its entirety.

What is claimed is:

1. An optical coherence tomographic imaging apparatus comprising:
    an image acquisition unit configured to acquire a plurality of images of a subject's eye at different times;
    a tomographic image acquisition unit configured to acquire a plurality of tomographic images of the subject's eye based on interference light obtained by interfering return light from the subject's eye irradiated with measuring light via a scanning unit and reference light corresponding to the measuring light;
    a movement amount acquisition unit configured to acquire the amount of subject's eye movement based on the plurality of images;
    a determination unit configured to determine whether the amount of subject's eye movement before a scan by the scanning unit exceeds a threshold value; and
    a control unit configured to control, in a case the amount of subject's eye movement before the scan is equal to or smaller than the threshold value, the scanning unit to perform scanning position correction between the scan and the next scan based on the amount of movement.

2. The optical coherence tomographic imaging apparatus according to claim 1, wherein, in a case the amount of subject's eye movement before the scan exceeds the threshold value, the control unit controls the scanning unit to restart at least one scan of the scanning unit from a scanning position before the scan.

3. The optical coherence tomographic imaging apparatus according to claim 1, wherein the image acquisition unit acquires the plurality of tomographic images of the subject's eye as the plurality of fundus images, and
wherein the movement amount acquisition unit acquires the amount of subject's eye movement based on the plurality of fundus images.

4. The optical coherence tomographic imaging apparatus according to claim 3, wherein the image acquisition unit acquires the plurality of fundus images by processing the plurality of tomographic images of the subject's eye.

5. The optical coherence tomographic imaging apparatus according to claim 1, wherein the movement amount acquisition unit acquires the amount of subject's eye rotation as the amount of movement based on the plurality of images, and
wherein the control unit controls the scanning unit to perform scanning position correction between the scan and the next scan based on the acquired amount of rotation.

6. The optical coherence tomographic imaging apparatus according to claim 1, further comprising:
a detection unit configured to detect a blink of the subject's eye before the scan based on the plurality of images,
wherein, in a case the blink is detected, the control unit controls the scanning unit to restart at least one scan of the scanning unit from a scanning position before the scan.

7. The optical coherence tomographic imaging apparatus according to claim 1, wherein the control unit controls the scanning unit to perform scanning position correction between one main scan and the next main scan of the scanning unit, and to suspend the scanning position correction during main scan of the scanning unit.

8. The optical coherence tomographic imaging apparatus according to claim 1, wherein the control unit controls the scanning unit to perform scanning position correction during sub scan of the scanning unit, and to suspend the scanning position correction during main scan of the scanning unit.

9. An optical coherence tomographic imaging apparatus comprising:
an image acquisition unit configured to acquire a plurality of images of the subject's eye at different times;
a tomographic image acquisition unit configured to acquire a plurality of tomographic images of the subject's eye based on interference light obtained by interfering return light from the subject's eye irradiated with measuring light via a scanning unit and reference light corresponding to the measuring light;
a movement amount acquisition unit configured to acquire the amount of subject's eye movement based on the plurality of images; and
a control unit configured to control, in a case the amount of subject's eye movement before a scan by the scanning unit exceeds the threshold value, the scanning unit to restart at least one scan of the scanning unit from a scanning position before the scan.

10. An optical coherence tomographic imaging apparatus comprising:
an image acquisition unit configured to acquire a plurality of images of the subject's eye at different times;
a tomographic image acquisition unit configured to acquire a plurality of tomographic images of the subject's eye based on interference light obtained by interfering return light from the subject's eye irradiated with measuring light via a scanning unit and reference light corresponding to the measuring light;
a detection unit configured to detect a blink of the subject's eye before a scan by the scanning unit based on the plurality of images; and
a control unit configured to control, in a case the blink is detected, the scanning unit to restart at least one scan of the scanning unit from a scanning position before the scan.

11. A method for controlling an optical coherence tomographic imaging apparatus for acquiring a plurality of tomographic images of the subject's eye based on interference light obtained by interfering return light from the subject's eye irradiated with measuring light via a scanning unit and reference light corresponding to the measuring light, the method comprising:
acquiring the amount of subject's eye movement based on a plurality of images of the subject's eye acquired at different times;
determining whether the amount of subject's eye movement before a scan by the scanning unit exceeds a threshold value; and
controlling, in a case the amount of subject's eye movement before the scan is equal to or smaller than the threshold value, the scanning unit to perform scanning position correction between the scan and the next scan based on the amount of movement.

12. The method for controlling the optical coherence tomographic imaging apparatus according to claim 11, wherein, in the control, in a case the amount of subject's eye movement before the scan exceeds the threshold value, the method controls the scanning unit to restart at least one scan of the scanning unit from a scanning position before the scan.

13. The method for controlling the optical coherence tomographic imaging apparatus according to claim 11, wherein the plurality of images is a plurality of fundus images of the subject's eye, and
wherein, in acquiring the amount of movement, the method acquires the amount of subject's eye movement based on the plurality of fundus images.

14. The method for controlling the optical coherence tomographic imaging apparatus according to claim 13, wherein the method acquires the plurality of fundus images by processing the plurality of tomographic images of the subject's eye.

15. The method for controlling the optical coherence tomographic imaging apparatus according to claim 11, wherein, in acquiring the amount of movement, the method acquires the amount of subject's eye rotation as the amount of movement based on the plurality of images, and
wherein, in the control, the method controls the scanning unit to perform scanning position correction between the scan and the next scan based on the acquired amount of rotation.

16. The method for controlling the optical coherence tomographic imaging apparatus according to claim 11, the method further comprising:
detecting a blink of the subject's eye before the scan based on the plurality of images,
wherein, in the control, in a case the blink is detected, the method controls the scanning unit to restart at least one scan of the scanning unit from a scanning position before the scan.

17. The method for controlling the optical coherence tomographic imaging apparatus according to claim 11, wherein, in the control, the method controls the scanning unit to perform scanning position correction between one main scan and the next main scan of the scanning unit, and to suspend the scanning position correction during main scan of the scanning unit.

18. The method for controlling the optical coherence tomographic imaging apparatus according to claim 11, in the control, the method controls the scanning unit to perform scanning position correction during sub scan of the scanning unit, and to suspend the scanning position correction during main scan of the scanning unit.

19. A method for controlling an optical coherence tomographic imaging apparatus for acquiring a plurality of tomographic images of the subject's eye based on interference light obtained by interfering return light from the subject's eye irradiated with measuring light via a scanning unit and reference light corresponding to the measuring light, the method comprising:
    acquiring the amount of subject's eye movement based on a plurality of images of the subject's eye acquired at different times; and
    controlling, in a case the amount of subject's eye movement before a scan by the scanning unit exceeds the threshold value, the scanning unit to restart at least one scan of the scanning unit from a scanning position before the scan.

20. A method for controlling an optical coherence tomographic imaging apparatus for acquiring a plurality of tomographic images of the subject's eye based on interference light obtained by interfering return light from the subject's eye irradiated with measuring light via a scanning unit and reference light corresponding to the measuring light, the method comprising:
    detecting a blink of the subject's eye before a scan by the scanning unit based on a plurality of images of the subject's eye acquired at different times; and
    controlling, in a case the blink is detected, the scanning unit to restart at least one scan of the scanning unit from a scanning position before the scan.

* * * * *